US012661326B2

(12) United States Patent
Sukuru et al.

(10) Patent No.: US 12,661,326 B2
(45) Date of Patent: Jun. 23, 2026

(54) COATED ENTERIC SOFTGEL CAPSULES

(71) Applicant: R.P. SCHERER TECHNOLOGIES, LLC, Carson City, NV (US)

(72) Inventors: Karunakar Sukuru, St. Petersburg, FL (US); Qi Fang, St. Petersburg, FL (US); Haitao Li, St. Petersburg, FL (US)

(73) Assignee: R.P. SCHERER TECHNOLOGIES, LLC, Carson City, NV (US)

( * ) Notice: Subject to any disclaimer, the term of this patent is extended or adjusted under 35 U.S.C. 154(b) by 0 days.

(21) Appl. No.: 18/819,242

(22) Filed: Aug. 29, 2024

(65) Prior Publication Data

US 2024/0423921 A1     Dec. 26, 2024

Related U.S. Application Data

(63) Continuation of application No. PCT/US2023/030040, filed on Aug. 11, 2023.

(60) Provisional application No. 63/397,558, filed on Aug. 12, 2022.

(51) Int. Cl.
A61K 9/48          (2006.01)

(52) U.S. Cl.
CPC .......... A61K 9/4891 (2013.01); A61K 9/4825 (2013.01)

(58) Field of Classification Search
None
See application file for complete search history.

(56) References Cited

U.S. PATENT DOCUMENTS

| | | |
|---|---|---|
| 2007/0098786 A1 | 5/2007 | Chidambaram et al. |
| 2007/0196463 A1 | 8/2007 | Podili et al. |
| 2018/0055776 A1 | 3/2018 | Draper et al. |
| 2023/0404927 A1* | 12/2023 | Sukuru .................. A61K 35/60 |

FOREIGN PATENT DOCUMENTS

| | | |
|---|---|---|
| WO | 2022104338 A1 | 5/2022 |

OTHER PUBLICATIONS

Felton, L., et al., International Journal of Pharmaceutics 113: 17 â 24 (1995). (Year: 1995).*
Eudragitâ® L30, retrieved from the Internet at https://www.stobec.com/DATA/PRODUIT/1598~v~data_8595.pdf, on Dec. 7, 2024. (Year: 2024).*
Handali, S., et al., Journal of Drug Delivery Science and Technology 47: 492 â 498 (2018). (Year: 2018).*
International Search Report and Written Opinion for International Application No. PCT/US2023/030040, mailed Nov. 20, 2023, 8 Pages.

* cited by examiner

*Primary Examiner* — David J Blanchard
*Assistant Examiner* — Daniel F Coughlin
(74) *Attorney, Agent, or Firm* — Lowenstein Sandler LLP

(57)          ABSTRACT

Disclosed herein is a softgel capsule including a fill material, shell composition and a coating having an enteric polymer, wherein the coating provides about 1% to about 10% weight gain of the capsule. The coating improves the robustness of enteric property and minimized the moisture absorption during dissolution of the softgel capsule.

21 Claims, 1 Drawing Sheet

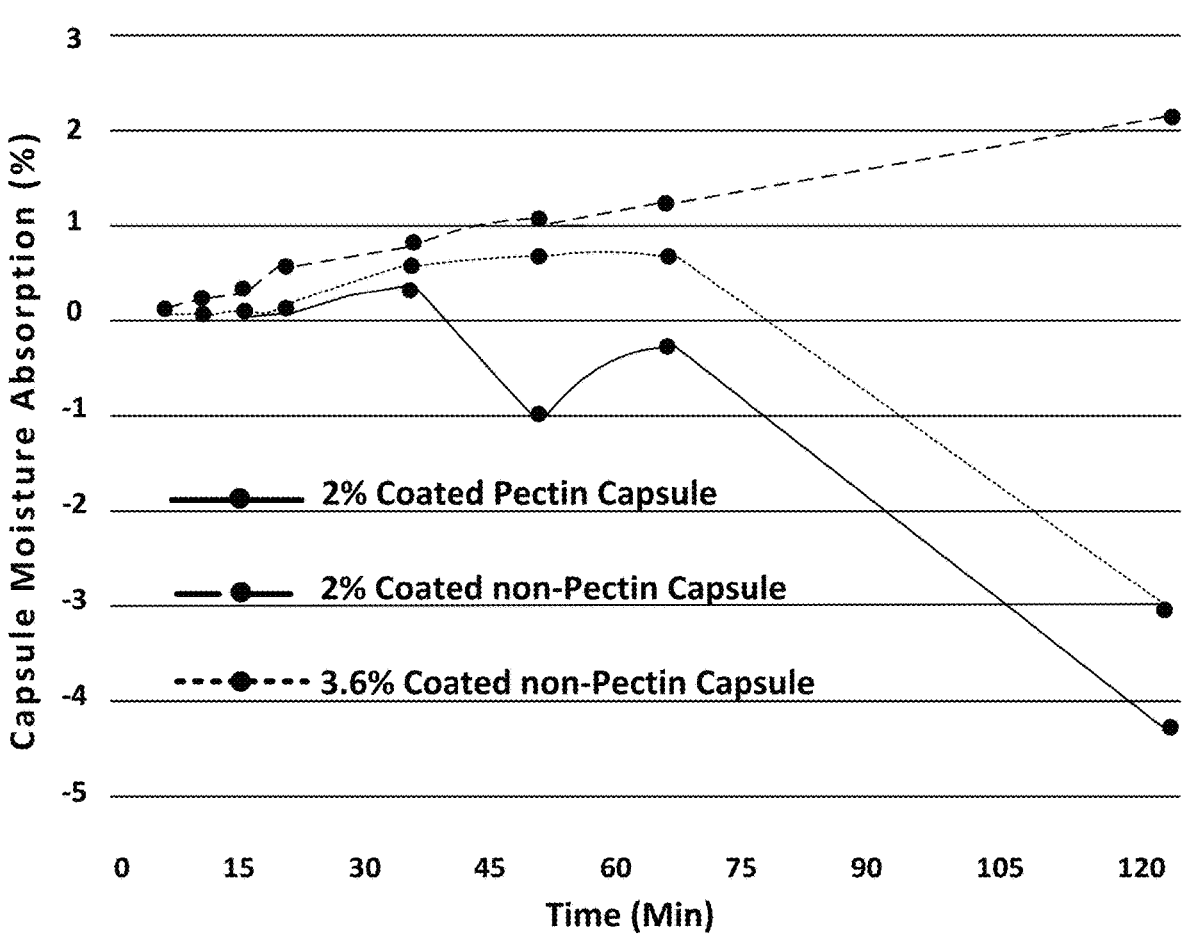
Capsules Moisture Absorption

COATED ENTERIC SOFTGEL CAPSULES

CROSS REFERENCE TO RELATED APPLICATION(S)

The present application claims priority to U.S. Provisional Patent Application No. 63/397,558 filed on Aug. 12, 2022, the entire contents of which are incorporated in its entirety.

FIELD OF THE INVENTION

The present invention relates to softgel capsules including a fill composition and a shell composition, wherein the shell composition includes pectin. The softgel capsule of the present invention further includes a coating comprising an enteric polymer.

BACKGROUND OF THE INVENTION

Soft capsules, in particular, soft gelatin capsules (or softgel capsules), provide a dosage form which is more readily accepted by patients, since the capsules are easy to swallow and need not be flavored in order to mask any unpleasant taste of the active agent. Softgel encapsulation of drugs further provides the potential to improve the bioavailability of the pharmaceutical agents. For example, active ingredients may be rapidly released in liquid form as soon as the gelatin shell ruptures.

Efforts have been made to create enteric dosage forms. Enteric dosage forms are designed to protect the contents of the dosage form from gastric conditions. For example, enteric dosage forms have been developed in which conventional enteric polymers (i.e., acid-insoluble polymers) are added in the capsule shell. However, the addition of conventional enteric polymers can lead to capsules that are prone to leaking due to insufficient sealing. Further, it has been found that the addition of enteric polymers in the capsule shell may cause the shell to absorb a significant quantity of water, which weakens the mechanical strength and could potentially affect the chemical stability of the drug substances.

Accordingly, there is currently a need for a softgel capsule that minimizes water uptake and to preserve the mechanical strength.

SUMMARY OF THE INVENTION

The present invention is directed to softgel capsules including a light weight enteric polymer coating. The softgel capsules of the present disclosure include a fill composition and a shell composition, wherein the shell composition includes pectin. The softgel capsule further has a coating including an enteric polymer. It has been found that including a light weight coating to softgel capsules improved the robustness of the enteric property. Using a light weight coating was also found to achieve a more uniform coating on the softgel capsule, resulting in more consistent performance of the dosage forms. Further, the coating also increases the pH threshold of the capsule, such that it may be delivered further in the digestive system, such as colonic delivery.

The present invention is also directed to a process of making enteric softgel capsules.

DESCRIPTION OF DRAWINGS

The present disclosure is illustrated by way of example, and not by way of limitation, in the figures of the accompanying drawings in which like references indicate similar elements. It should be noted that different references to "an" or "one" embodiment in this disclosure are not necessarily to the same embodiment, and such references mean at least one.

FIG. 1 illustrates the capsule moisture absorption results of coated softgel capsules according to an embodiment of the present invention.

DETAILED DESCRIPTION OF THE INVENTION

The present disclosure advances the state of the art by developing enteric oral dosage forms, in particular, enteric softgel capsules, that improves the enteric property of a softgel capsule. The enteric softgel capsules of the present invention do not dissolve in a gastric environment of the stomach, but rather dissolve further in the digestive system, for example, in the intestines or colon. Such mechanism is beneficial for delivery of active ingredients that may cause stomach irritation or are sensitive to the acidic environment of the stomach.

As used herein, the term "enteric" is used to refer to the dissolution or disintegration resistant property of a substance such that dissolution or disintegration does not occur in a gastric environment. For example, the embodiments described herein include an enteric shell composition that dissolves in biological, artificial or simulated intestinal fluid rather than in biological, artificial or simulated gastric fluid. The embodiments described herein also include a coating having an enteric polymer.

As used herein, "pharmaceutically active ingredient" refers to a drug or compound that may be used in the diagnosis, cure, mitigation, treatment, or prevention of a condition. The term "condition" or "conditions" refers to those medical conditions that can be treated or prevented by administration to a subject of an effective amount of an active agent. Exemplary non-limiting conditions that may benefit from enteric softgel capsules may include, without limitations, capsules containing lactic acid bacteria, fish oil capsules, proton pump inhibitors, aspirin and similar products.

As used herein, the term "active ingredient" refers to any material that is intended to produce a therapeutic, prophylactic, or other intended effect, whether or not approved by a government agency for that purpose. This term with respect to a specific agent includes the pharmaceutically active agent, and all pharmaceutically acceptable salts, solvates and crystalline forms thereof, where the salts, solvates and crystalline forms are pharmaceutically active.

Any pharmaceutically active ingredient may be used for purposes of the present invention, including both those that are water-soluble and those that are poorly soluble in water. Suitable pharmaceutically active ingredients include, without limitation, analgesics and anti-inflammatory agents, antacids, anthelmintic, anti-arrhythmic agents, anti-bacterial agents, anti-coagulants, anti-depressants, anti-diabetics, anti-diarrheal, anti-epileptics, anti-fungal agents, anti-gout agents, anti-hypertensive agents, anti-malarial, anti-migraine agents, anti-muscarinic agents, anti-neoplastic agents and immunosuppressants, anti-protozoal agents, anti-rheumatics, anti-thyroid agents, antivirals, anxiolytics, sedatives, hypnotics and neuroleptics, beta-blockers, cardiac inotropic agents, corticosteroids, cough suppressants, cytotoxics, decongestants, diuretics, enzymes, anti-parkinsonian agents, gastro-intestinal agents, histamine receptor antagonists, lipid regulating agents, local anesthetics, neuromuscular agents, nitrates and anti-anginal agents, nutritional agents, opioid analgesics, oral vaccines, proteins, peptides and recombinant drugs, sex hormones and contraceptives, spermicides, stimulants, and combinations thereof. In certain embodiments, the present invention is also directed to methods of treatment utilizing any of the active ingredients disclosed herein to treat a disease or condition that can be treated by the active ingredient.

In some embodiments, the active pharmaceutical ingredient may be selected, without limitations, from the group consisting of dabigatran, dronedarone, ticagrelor, iloperidone, ivacaftor, midostaurine, asimadoline, beclomethasone, apremilast, sapacitabine, linsitinib, abiraterone, vitamin D analogs (e.g., calcifediol, calcitriol, paricalcitol, doxercalciferol), COX-2 inhibitors (e.g., celecoxib, valdecoxib, rofecoxib), tacrolimus, testosterone, lubiprostone, pharmaceutically acceptable salts thereof, and combinations thereof.

In some embodiments, the lipids in the dosage form may be selected, without limitations, from the group consisting of, almond oil, argan oil, avocado oil, borage seed oil, canola oil, cashew oil, castor oil, hydrogenated castor oil, cocoa butter, coconut oil, colza oil, corn oil, cottonseed oil, grape seed oil, hazelnut oil, hemp oil, hydroxylated lecithin, lecithin, linseed oil, macadamia oil, mango butter, manila oil, mongongo nut oil, olive oil, palm kernel oil, palm oil, peanut oil, pecan oil, perilla oil, pine nut oil, pistachio oil, poppy seed oil, pumpkin seed oil, rice bran oil, safflower oil, sesame oil, shea butter, soybean oil, sunflower oil, hydrogenated vegetable oil, walnut oil, and watermelon seed oil. Other oil and fats may include, but not be limited to, fish oil (omega-3), krill oil, animal or vegetable fats, e.g., in their hydrogenated form, free fatty acids and mono-, di-, and tri-glycerides with C8-, C10-, C12-, C14-, C16-, C18-, C20- and C22-fatty acids, and combinations thereof.

According to certain embodiments, active agents may include lipid-lowering agents including, but not limited to, statins (e.g., lovastatin, simvastatin, pravastatin, fluvastatin, atorvastatin, rosuvastatin, and pitavastatin), fibrates (e.g, clofibrate, ciprofibrate, bezafibrate, fenofibrate, and gemfibrozil), niacin, bile acid sequestrants, ezetimibe, lomitapide, phytosterols, and the pharmaceutically acceptable salts, hydrates, solvates and prodrugs thereof, mixtures of any of the foregoing, and the like.

Suitable nutraceutical active agents may include, but are not limited to, 5-hydroxytryptophan, acetyl L-carnitine, alpha lipoic acid, alpha-ketoglutarates, bee products, betaine hydrochloride, bovine cartilage, caffeine, cetyl myristoleate, charcoal, chitosan, choline, chondroitin sulfate, coenzyme Q10, collagen, colostrum, creatine, cyanocobalamin (Vitamin 812), dimethylaminoethanol, fumaric acid, germanium sequioxide, glandular products, glucosamine HCl, glucosamine sulfate, hydroxyl methyl butyrate, immunoglobulin, lactic acid, L-Carnitine, liver products, malic acid, maltose-anhydrous, mannose (d-mannose), methyl sulfonyl methane, phytosterols, picolinic acid, pyruvate, red yeast extract, S-adenosylmethionine, selenium yeast, shark cartilage, theobromine, vanadyl sulfate, and yeast.

Suitable nutritional supplement active agents may include vitamins, minerals, fiber, fatty acids, amino acids, herbal supplements or a combination thereof.

Suitable vitamin active agents may include, but are not limited to, the following: ascorbic acid (Vitamin C), B vitamins, biotin, fat soluble vitamins, folic acid, hydroxycitric acid, inositol, mineral ascorbates, mixed tocopherols, niacin (Vitamin B3), orotic acid, para-aminobenzoic acid, panthothenates, panthothenic acid (Vitamin B5), pyridoxine hydrochloride (Vitamin B6), riboflavin (Vitamin B2), synthetic vitamins, thiamine (Vitamin B1), tocotrienols, vitamin A, vitamin D, vitamin E, vitamin F, vitamin K, vitamin oils and oil soluble vitamins.

Suitable herbal supplement active agents may include, but are not limited to, the following: arnica, bilberry, black cohosh, cat's claw, chamomile, echinacea, evening primrose oil, fenugreck, flaxseed, feverfew, garlic, ginger root, ginko biloba, ginseng, goldenrod, hawthorn, kava-kava, licorice, milk thistle, psyllium, rauowolfia, senna, soybean, St. John's wort, saw palmetto, turmeric, valerian.

Minerals active agents may include, but are not limited to, the following: boron, calcium, chelated minerals, chloride, chromium, coated minerals, cobalt, copper, dolomite, iodine, iron, magnesium, manganese, mineral premixes, mineral products, molybdenum, phosphorus, potassium, selenium, sodium, vanadium, malic acid, pyruvate, zinc and other minerals.

Examples of other possible active agents include, but are not limited to, antihistamines (e.g., ranitidine, dimenhydrinate, diphenhydramine, chlorpheniramine and dexchlorpheniramine maleate), non-steroidal anti-inflammatory agents (e.g., aspirin, celecoxib, Cox-2 inhibitors, diclofenac, benoxaprofen, flurbiprofen, fenoprofen, flubufen, indoprofen, piroprofen, carprofen, oxaprozin, pramoprofen, muroprofen, trioxaprofen, suprofen, aminoprofen, fluprofen, bucloxic acid, indomethacin, sulindac, zomepirac, tiopinac, zidometacin, acemetacin, fentiazac, clidanac, oxpinac, meclofenamic acid, flufenamic acid, niflumic acid, tolfenamic acid, diflurisal, flufenisal, piroxicam, sudoxicam, isoxicam, aceclofenac, aloxiprin, azapropazone, benorilate, bromfenac, carprofen, choline magnesium salicylate, diflunisal, etodolac, etoricoxib, faislamine, fenbufen, fenoprofen, flurbiprofen, ibuprofen, indometacin, ketoprofen, ketorolac, lornoxicam, loxoprofen, meloxicam, mefenamic acid, metamizole, methyl salicylate, magnesium salicylate, nabumetone, naproxen, nimesulide, oxyphenbutazone, parecoxib, phenylbutazone, salicyl salicylate, sulindac, sulfinpyrazone, tenoxicam, tiaprofenic acid, tolmetin. pharmaceutically acceptable salts thereof and mixtures thereof) and acetaminophen, anti-emetics (e.g., metoclopramide, methylnaltrexone), anti-epileptics (e.g., phenyloin, meprobmate and nitrazepam), vasodilators (e.g., nifedipine, papaverine, diltiazem and nicardipine), anti-tussive agents and expectorants (e.g. codeine phosphate), anti-asthmatics (e.g. theophylline), antacids, anti-spasmodics (e.g. atropine, scopolamine), antidiabetics (e.g., insulin), diuretics (e.g., ethacrynic acid, bendrofluthiazide), anti-hypotensives (e.g., propranolol, clonidine), antihypertensives (e.g., clonidine, methyldopa), bronchodilatiors (e.g., albuterol), steroids (e.g., hydrocortisone, triamcinolone, prednisone), antibiotics (e.g., tetracycline), antihemorrhoidals, hypnotics, psychotropics, antidiarrheals, mucolytics, sedatives, decongestants (e.g. pseudoephedrine), laxatives, vitamins, stimulants (including appetite suppressants such as phenylpropanolamine) and cannabinoids, as well as pharmaceutically acceptable salts, hydrates, solvates, and prodrugs thereof.

The active agent that may also be a benzodiazepine, barbiturate, stimulants, or mixtures thereof. The term "benzodiazepines" refers to a benzodiazepine and drugs that are derivatives of a benzodiazepine that are able to depress the central nervous system. Benzodiazepines include, but are not limited to, alprazolam, bromazepam, chlordiazepoxide, clorazepate, diazepam, estazolam, flurazepam, halazepam, ketazolam, lorazepam, nitrazepam, oxazepam, prazepam, quazepam, temazepam, triazolam, methylphenidate as well as pharmaceutically acceptable salts, hydrates, solvates, prodrugs and mixtures thereof. Benzodiazepine antagonists that can be used as active agent include, but are not limited to, flumazenil as well as pharmaceutically acceptable salts, hydrates, solvates and mixtures thereof.

The term "barbiturates" refers to sedative-hypnotic drugs derived from barbituric acid (2, 4, 6,-trioxohexahydropyrimidine). Barbiturates include, but are not limited to, amobarbital, aprobarbotal, butabarbital, butalbital, methohexital, mephobarbital, metharbital, pentobarbital, phenobarbital, secobarbital as well as pharmaceutically acceptable salts, hydrates, solvates, prodrugs, and mixtures thereof. Barbiturate antagonists that can be used as active agent include, but are not limited to, amphetamines as well as pharmaceutically acceptable salts, hydrates, solvates and mixtures thereof.

The term "stimulants" includes, but is not limited to, amphetamines such as dextroamphetamine resin complex, dextroamphetamine, methamphetamine, methylphenidate, as well as pharmaceutically acceptable salts, hydrates, and solvates and mixtures thereof. Stimulant antagonists that can be used as active agent include, but are not limited to, benzodiazepines, as well as pharmaceutically acceptable salts, hydrates, solvates and mixtures thereof.

The dosage forms according to the disclosure include various active agents and their pharmaceutically acceptable salts thereof. Pharmaceutically acceptable salts include, but are not limited to, inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate, and the like; amino acid salts such as arginate, asparginate, glutamate and the like, and metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like.

As used herein, the terms "therapeutically effective" and an "effective amount" refer to the amount of active agent or the rate at which it is administered which is needed to produce a desired therapeutic result.

As used herein, "shell" or "shell composition" refers to the shell of a softgel capsule which encapsulates a fill material.

As used herein, "conventional enteric polymers" refer to, but are not limited to, acrylic and methacrylic acid polymers, which may be available under the tradename EUDRAGIT® and other conventional acid insoluble polymers, e.g., methyl acrylate-methacrylic acid copolymers. Other conventional acid insoluble polymers include, without limitation, cellulose acetate succinate, cellulose acetate phthalate, cellulose acetate butyrate, hydroxypropyl methyl cellulose phthalate, hydroxy propyl methyl cellulose acetate succinate (hypermellose acetate succinate), polyvinyl acetate phthalate (PVAP), algenic acid salts such as sodium alginate and potassium alginate, stearic acid, and shellac. In some embodiments, the enteric shell composition of the present invention does not include an acid insoluble polymer. In other words, the enteric shell composition and the enteric softgel capsule are "free or substantially free of conventional enteric polymers."

As used herein, "free or substantially free," refers to a composition that comprises less than about 1 wt %, less than about 0.5 wt %, less than about 0.25 wt %, less than about 0.1 wt %, less than about 0.05 wt %, less than about 0.01 wt %, or 0 wt % of said component.

All references to wt % throughout the specifications and the claims refer to the weight of the component in reference to the weight of the entire composition and may also be designated as w/w.

As used herein, "fill material" or "fill" refers to the composition that is encapsulated by the enteric capsule shell and contains at least one pharmaceutically active ingredient.

As used herein, "delayed release" refers to releasing the active agent after passing through the stomach.

As used herein, "about" refers to any values that are within a variation of +10%, such that "about 10" would include from 9 to 11. As used herein, "a," "an," or "the" refers to one or more, unless otherwise specified. Thus, for example, reference to "an excipient" includes a single excipient as well as a mixture of two or more different excipients, and the like.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

The use of any and all examples, or exemplary language (e.g., "such as") provided herein, is intended merely to illuminate certain materials and methods and does not pose a limitation on scope. No language in the specification should be construed as indicating any non-claimed element as essential to the practice of the disclosed materials and methods.

According to one embodiment, a delayed release softgel capsule includes a fill material including an active agent, a shell composition including pectin, and a coating including an enteric polymer.

In some embodiments of the capsule, the coating of the softgel capsule may provide a weight gain of about 0.1% to about 10%, about 0.5% to about 5%, about 1% to about 10%, about 1% to about 5%, about 1% to about 3%, or about 2% to about 5% of the capsule.

Suitable fill materials comprise at least one pharmaceutically active ingredient and can be made according to known methods. In addition to the at least one pharmaceutically active ingredient, suitable fill materials may comprise additional fill components such as flavoring agents, sweetening agents, coloring agents and fillers or other pharmaceutically acceptable excipients or additives such as synthetic dyes and mineral oxides. Suitable amounts of pharmaceutically active ingredient and pharmaceutically acceptable excipients can be readily determined by one of ordinary skill in the art.

In some embodiments, the pectin in the shell composition may be a low methoxy pectin. In an embodiment, the low methoxy pectin may be LM Pectin (P-25), LM Pectin (445C), LM Pectin (100C) or a combination thereof. In another embodiment, the pectin may be amidated pectin or non-amidated pectin. The addition of pectin contributes to the enteric nature of the dosage form. However, too much pectin in the dosage form may reduce the gel strength of the softgel capsule which may in turn adversely affect the scalability of the softgel capsule. Therefore, pectin may be added to the dosage form at a concentration that is sufficiently high to form an enteric dosage form and at the same time is sufficiently low to mitigate the reduction in gel strength. In an embodiment, an amount of pectin in the enteric shell composition is about 2 wt % to about 30 wt %, about 2 wt % to about 25 wt %, about 2 wt % to about 20 wt %, from about 3 wt % to about 15 wt %, from about 3 wt % to about 5.5 wt %, from about 5 wt % to about 10 wt %, about 2.5 wt % to about 20 wt %, about 5 wt % to about 18 wt %, 7.5 wt % to about 15 wt %, or about 10 wt % to about 12 wt % based on total weight of the shell composition. The degree of esterification of the pectin incorporated in the shell composition may be lower than about 50%, or may range from about 10% to about 50%, from about 20% to about 40%, or from about 25% to about 35%.

In some embodiments of the capsule, the shell composition may further include a plasticizer. The plasticizer may include glycerol, glycerin, sorbitol, sorbitol sorbitan solution, triacetin, polysorbate, or combinations thereof. In one embodiment, the plasticizer may include glycerin and sorbitol sorbitan solution. In some embodiments, the polysorbate may include polysorbate 20 also known as Tween 20, polysorbate 80 also known as Tween 80 or combinations thereof. Other suitable plasticizers may include, but not be limited to, sugar alcohol plasticizer such as isomalt, maltitol, xylitol, erythritol, adonitol, dulcitol, pentacrythritol, or mannitol; or polyol plasticizer such as diglycerin, ethylene glycol, diethylene glycol, tricthyleneglycol, tetraethylene glycol, dipropylene glycol, a polyethylene glycol up to 10,000 MW, neopentyl glycol, propylene glycol, 1,3-propanediol, 2-methyl-1,3-propanediol, trimethylolpropane, a polyether polyol, ethanol amines; and mixtures thereof. Other exemplary plasticizers may also include, without limitations, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, citrate ester-type plasticizers, and triacetin. Such plasticizers may include 1,2-butylene glycol, 2,3-butylene glycol, styrene glycol, monopropylene glycol monoisopropyl ether, propylene glycol monoethyl ether, ethylene glycol monoethyl ether, diethylene glycol monocthyl ether, sorbitol lactate, ethyl lactate, butyl lactate, ethyl glycolate, dibutyl sebacate, acetyltributylcitrate, triethyl citrate, glyceryl monostearate, acetyl triethyl citrate, tributyl citrate and allyl glycolate, and mixtures thereof.

In some embodiments, the amount of plasticizer may be in an amount of about 5 wt % to about 75 wt %, about 2 wt % to about 40 wt %, about 2 wt % to about 15 wt %, about 4 wt % to about 12 wt %, about 5 wt % to about 60 wt %, about 10 wt % to about 55 wt %, about 15 wt % to about 50 wt %, about 20 wt % to about 45 wt %, or about 25 wt % to about 35 wt % based on total weight of the shell composition.

In some embodiments, the plasticizer may be glycerin. The glycerin may be included in an amount of about 5 wt % to about 30 wt %, about 8 wt % to about 26 wt %, about 12 wt % to about 22 wt %, or about 15 wt % to about 22 wt % based on total weight of the shell composition.

In some embodiments the plasticizer may be sorbitol sorbitan solution. The sorbitol sorbitan solution may be included in an amount of about 2 wt % to about 40 wt %, about 5 wt % to about 36 wt %, about 8 wt % to about 30 wt %, about 10 wt % to about 27 wt %, or about 15 wt % to about 22 wt %, based on total weight of the shell composition.

In some embodiments of the softgel capsule, the shell composition may further include gelatin. The gelatin may include Type A gelatin, Type B gelatin, a hide gelatin and/or a bone gelatin used alone or in combination. In one embodiment, the gelatin is a 250 bloom gelatin. In another embodiment, there is only one type of gelatin. In yet another embodiment, the gelatin is a combination of at least two types of gelatins. In an embodiment, the amount of gelatin in the enteric shell composition is about 10 wt % to about 80 wt %, about 15 wt % to about 60 wt %, about 20 wt % to about 55 wt %, about 25 wt % to about 50 wt %, about 30 wt % to about 45 wt %, or about 35 wt % to about 40 wt % based on total weight of the shell composition.

In some embodiments, the shell composition of the soft-gel capsule may include a cellulose derivate, such as hydroxypropyl methylcellulose (HPMC). In an embodiment, the amount of cellulose derivative (e.g., HPMC) in the shell composition is about 0.15 wt % to about 4.0 wt %, more preferably from about 0.20 wt % to about 2.0 wt %, and most preferably from about 0.25 wt % to about 1.4 wt %. In some embodiments, the enteric capsule shell composition may comprise HPMC, methyl cellulose (MC), hydroxypropylcellulose (HPC), or combinations thereof. The cellulose derivative may be added to the shell composition to mitigate potential reduction in gel strength. The concentration of cellulose derivative in the enteric shell composition may be in an effective amount to improve the gel strength but not so high that it would interfere with the seal.

In some embodiments, the shell composition of the soft-gel capsule may also include gellan gum, dextrose, water or a combination thereof. In some embodiments, the amount of dextrose may be about 0.001 wt % to about 10 wt %, about 0.001 wt % to about 5 wt %, about 0.01 wt % to about 4.5 wt %, about 0.01 wt % to about 4 wt %, about 0.1 wt % to about 3 wt %, or about 1 wt % to about 2.5 wt % based on total weight of the shell composition.

In an embodiment, the shell composition of the softgel capsule may optionally comprise additional agents such as coloring agents, flavorings agents, sweetening agents, fillers, antioxidants, diluents, pH modifiers or other pharmaceutically acceptable excipients or additives such as synthetic dyes and mineral oxides.

Exemplary suitable coloring agents may include, but not be limited to, colors such as e.g., white, black, yellow, blue, green, pink, red, orange, violet, indigo, and brown. In specific embodiments, the color of the dosage form can indicate the contents (e.g., one or more active ingredients) contained therein.

Exemplary suitable flavoring agents may include, but not be limited to, "flavor extract" obtained by extracting a part of a raw material, e.g., animal or plant material, often by using a solvent such as ethanol or water; natural essences obtained by extracting essential oils from the blossoms, fruit, roots, etc., or from the whole plants.

Additional exemplary flavoring agents that may be in the dosage form may include, but not be limited to, breath freshening compounds like menthol, spearmint, and cinnamon, coffee beans, other flavors or fragrances such as fruit flavors (e.g., cherry, orange, grape, etc.), especially those used for oral hygiene, as well as actives used in dental and oral cleansing such as quaternary ammonium bases. The effect of flavors may be enhanced using flavor enhancers like tartaric acid, citric acid, vanillin, or the like.

Exemplary sweetening agents may include, but not be limited to, one or more artificial sweeteners, one or more natural sweeteners, or a combination thereof. Artificial sweeteners include, e.g., acesulfame and its various salts such as the potassium salt (available as Sunett®), alitame, aspartame (available as NutraSwect® and Equal®), salt of aspartame-acesulfame (available as Twinsweet®), neohesperidin dihydrochalcone, naringin dihydrochalcone, dihydrochalcone compounds, neotame, sodium cyclamate, saccharin and its various salts such as the sodium salt (available as Sweet'N Low®), *stevia*, chloro derivatives of sucrose such as sucralose (available as Kaltame® and Splenda®), and mogrosides. Natural sweeteners include, e.g., glucose, dextrose, invert sugar, fructose, sucrose, glycyrrhizin; monoammonium glycyrrhizinate (sold under the trade name MagnaSweet®); *Stevia rebaudiana* (Stevioside), natural intensive sweeteners, such as Lo Han Kuo, polyols such as sorbitol, mannitol, xylitol, erythritol, and the like.

In some embodiments, the enteric polymer of the coating may be an acrylic polymer, a methacrylic acid polymer, cellulose acetate succinate, cellulose acetate phthalate, cellulose acetate butyrate, hydroxypropyl methyl cellulose phthalate, hydroxy propyl methyl cellulose acetate succinate (hypermellose acetate succinate), polyvinyl acetate phthalate (PVAP), algenic acid salt, such as sodium alginate, potassium alginate, stearic acid, shellac or a combination thereof. In some embodiments, the enteric polymer may be an acrylic polymer, a methacrylic acid polymer or a combination thereof. In some embodiments, the enteric polymer may be an aqueous dispersion of an anionic copolymer based on methyl acrylate, methyl methacrylate and methacrylic acid.

In some embodiments of the delayed release softgel capsule, the coating may further include a plasticizer. The plasticizer may be a glyceride, triethyl citrate or a combination thereof.

In some embodiments, the enteric polymer in the coating is in an amount of about 10 wt % to about 60 wt %, about 15 wt % to about 50 wt %, about 20 wt % to about 40 wt %, about 25 wt % to about 35 wt %, or about 30 wt % based on total weight of the coating. In some embodiments, the amount of plasticizer in the coating may be in an amount of about 2 wt % to about 10 wt %, about 3 wt % to about 9 wt %, about 4 wt % to about 8 wt %, or about 5 wt % based on total weight of the coating.

In some embodiments, the softgel capsule may have a dosing of omega-3 in an amount of about 100 mg to about 1000 mg, about 150 mg to about 900 mg, about 200 mg to about 800 mg, about 300 mg to about 700 mg, about 350 mg to about 600 mg, or about 400 mg to about 500 mg per dose.

In some embodiments, the delayed release softgel capsule may be tested in a disintegration test performed in a basket-rack assembly NT-40H model apparatus in a 1000 mL beaker at about 37° C.±2° C. (described in more detail below). The enteric softgel capsule according to this embodiment may remain intact for about one hour, about two hours, about three hours, about four hours, about five hours, or at least about 1 hour, at least about 2 hours, at least about 3 hours, at least about 4 hours, at least about 5 hours, or at least about 6 hours, or about 1 hour to about 6 hours, about 1 hour to about 4 hours, or about 1 hour to about 2 hours in acidic medium. In some embodiments, the softgel capsule may disintegrate in about 30 minutes or less in intestinal fluid, in about 20 minutes or less, in about 10 minutes or less, in about 5 minutes or less. In certain embodiments, the above results may also be achieved for a softgel capsule under accelerated stability conditions of 25° C./60% RH, 30° C./65% RH, or 40° C./75% RH at 1 month, 3 months, 6 months, 12 months, 18 months, 22 months, or 24 months.

Disintegration tests performed herein are harmonized with the European Pharmacopoeia and the U.S. Pharmacopoeia for enteric coated preparations. The apparatus used for the disintegration tests is of model NT-40H (manufactured by Toyama Sangyo Co. Ltd.). The apparatus being a basket-rack assembly, a 1000-mL, low form beaker, 138 to 160 mm in height and having an inside diameter of 97 to 115 mm for the immersion fluid, a thermostatic arrangement for heating the fluid between 35° C. and 39° C., and a device for raising and lowering the basket in the immersion fluid at a constant frequency rate between 29 and 32 cycles per minute through a distance of not less than 53 mm and not more than 57 mm. The volume of the fluid in the vessel is such that at the highest point of the upward stroke the wire mesh remains at least 15 mm below the surface of the fluid and descends to not less than 25 mm from the bottom of the vessel on the downward stroke. At no time should the top of the basket-rack assembly become submerged. The time required for upward stroke is equal to the time required for the downward stroke, and the change in the stroke direction is a smooth transition, rather than an abrupt reversal of motion. The basket-rack assembly moves vertically along its axis. There is no appreciable horizontal motion or movement of the axis from the vertical.

The disintegration tests disclosed herein were performed at about 37° C.±2° C. at a volume of fluid of 1000 mL. Disintegration test fluid 1 (also referred to herein as "artificial gastric juice") was 2 g/L sodium chloride-hydrochloric acid solution having a pH of 1.2. Disintegration test fluid 2 (also referred to herein as "artificial intestinal fluid") was 0.2 mol/L potassium dihydrogen phosphate-0.2 mol/L sodium hydroxide solution having a pH of 6.8.

The disintegration test with the first fluid was carried out for about 120 minutes by placing one unit in each of the six tubes of the basket, immersing the basket (and consequently the units) in the first test fluid, and lifting the basket from the fluid to observe whether the units disintegrated. Disintegration is defined as that state at which the unit is broken or the enteric shell composition is ruptured or broken. The test is met if none of the six units is disintegrated. A similar test is performed with the second disintegration test fluid for the selected duration.

In some embodiments, the disintegration test may be performed for about 150 minutes, about 120 minutes, about 105 minutes, about 90 minutes, about 75 minutes, about 60 minutes, about 45 minutes, about 30 minutes, about 15 minutes, about 10 minutes, or about 5 minutes.

In certain embodiments, a two-stage disintegration test may be performed on the softgel capsule of the present disclosure. Under the two-stage disintegration test, the softgel capsule is subjected to an acidic medium (pH=1.2) followed by a buffer medium (pH=6.8). When exposed to both the acidic and buffer medium, the softgel capsule may remain intact for at least about 1 hour, at least about 2 hours, at least about 3 hours, at least about 4 hours, at least about 5 hours, at least about 6 hours, or for about 1 hour to 6 hours, about 1 hour to about 5 hours, about 1 hour to about 4 hours, about 1 hour to about 3 hours, or about 1 hour to about 2 hours. In certain embodiments, the above results may also be achieved for a softgel capsule under accelerated storage conditions of 25° C./60% RH, 30° C./65% RH, or 40° C./75% RH at 1 month, 3 months, 6 months, 12 months, 18 months, 22 months, or 24 months. In certain embodiments, after any of the accelerated storage conditions disclosed herein, the intact time does not change from time 0 by more than 20%, by more than 10% or by more than 5% at 1 hour, 4 hours or 8 hours.

In certain embodiments, a two-stage disintegration test may be performed on the softgel capsule of the present disclosure. Under the two-stage disintegration test, the softgel capsule is subjected to an acidic medium (pH=1.2) followed by a buffer medium (pH=7.5). When exposed to both the acidic and buffer medium, the softgel capsule may remain intact for at least about 1 hour, at least about 2 hours, at least about 3 hours, at least about 4 hours, at least about 5 hours, at least about 6 hours, or for about 1 hour to 6 hours, about 1 hour to about 5 hours, about 1 hour to about 4 hours, about 1 hour to about 3 hours, or about 1 hour to about 2 hours. In certain embodiments, the above results may also be achieved for a softgel capsule under accelerated storage conditions of 25° C./60% RH, 30° C./65% RH, or 40° C./75% RH at 1 month, 3 months, 6 months, 12 months, 18 months, 22 months, or 24 months. In certain embodiments, after any of the accelerated storage conditions disclosed herein, the intact time does not change from time 0 by more than 20%, by more than 10% or by more than 5% at 1 hour, 4 hours or 8 hours.

In some embodiments, the disintegration test may be performed using a buffer having a pH of 7.5. Under these conditions, the softgel capsule may disintegrate in about 30 minutes or less, about 25 minutes or less, about 20 minutes or less, about 15 minutes, about 10 minutes or less, or about 5 minutes or less. In some embodiments, the disintegrates may be performed using a buffer having a pH of 7.5 and under accelerated storage conditions of 5° C./60% RH, 30° C./65% RH, or 40° C./75% RH at 1 month, 3 months, 6 months, 12 months, 18 months, 22 months, or 24 months. Under these conditions, the softgel capsule may disintegrate in about 45 minutes or less, about 40 minutes or less, about 35 minutes or less, about 30 minutes or less, about 25 minutes or less, about 20 minutes or less, about 15 minutes or less, about 10 minutes or less, or about 5 minutes or less.

In some embodiments, the softgel capsule may be tested under a moisture absorption test by exposing the softgel capsule to an aqueous medium. The softgel capsule may have a moisture absorption of less than 2%, less than 1.5%, less than 1%, less than 0.8%, less than 0.6%, less than 0.5%, less than 0.4%, less than 0.3%, less than 0.2%, less than 0.1%, or less than 0.05% after exposing the softgel capsule after 5 minutes, 10 minutes, 15 minutes, 30 minutes, 45 minutes, 60 minutes, or 120 minutes. In certain embodiments, the above results may also be achieved for a softgel capsule under accelerated storage conditions of 25° C./60% RH, 30° C./65% RH, or 40° C./75% RH at 1 month, 3 months, 6 months, 12 months, 18 months, 22 months, or 24 months.

Encapsulation of the fill material can be accomplished in any conventional manner. As an example, a rotary die encapsulation may be used.

According to an embodiment, an enteric softgel capsule is prepared by the process comprising the steps of: preparing the fill material, the fill material including an active agent; encapsulating the fill material in a shell composition, where the shell composition includes pectin, and thus forms a softgel capsule. The capsule is then coated with a coating composition comprising an enteric polymer, such that the capsule has about 1% to about 10% weight gain.

The method of preparing the softgel capsule includes preparing the shell composition, wherein the shell composition may include pectin, a plasticizer, gelatin, gellan gum, dextrose, water or a combination thereof as described herein.

The coating composition is then prepared by preparing a coating suspension including an enteric polymer, a plasticizer, water or a combination thereof. In certain embodiments, the enteric polymer may include an anionic copolymer based on methyl acrylate.

In certain embodiments, the present invention is directed to the one or more of the following lists of items:

1. A delayed release softgel capsule may include: a fill material, wherein the fill material comprises an active agent; a shell composition, wherein the shell composition comprises pectin; and a coating comprising an enteric polymer.

2. The delayed release softgel capsule of item 1, wherein the coating provides a weight gain of about 1% to about 10 wt %, or about 2% to about 5% of the capsule.

3. The delayed release softgel capsule of items 1 or 2, wherein the shell composition further comprises a plasticizer.

4. The delayed release softgel capsule of item 3, wherein the plasticizer comprises glycerol, glycerin, sorbitol, sorbitol sorbitan solution, triacetin, polysorbate, or combinations thereof.

5. The delayed release softgel capsule of any one of items 3-4, wherein the plasticizer comprises glycerin and sorbitol sorbitan solution.

6. The delayed release softgel capsule of item 4, wherein the polysorbate comprises Tween 20, Tween 80 or combinations thereof.

7. The delayed release softgel capsule of any one of the preceding items, wherein the shell composition further comprises gelatin.

8. The delayed release softgel capsule of item 7, wherein the gelatin is selected from the group consisting of Type A gelatin, Type B gelatin, and mixtures thereof.

9. The delayed release softgel capsule of item 7, wherein the gelatin is selected from the group consisting of fish gelatin, hide gelatin, bone gelatin and mixtures thereof.

10. The delayed release softgel capsule of any one of the preceding items, wherein the shell composition further comprises gellan gum.

11. The delayed release softgel capsule of any one of the preceding items, wherein the shell composition further comprises dextrose.

12. The delayed release softgel capsule of any one of the preceding items, wherein the shell composition further comprises water.

13. The delayed release softgel capsule of any one of the preceding items, wherein the pectin is a low methoxy pectin.

14. The delayed release softgel capsule of any one of the preceding items, wherein the enteric polymer is an acrylic polymer, a methacrylic acid polymer, cellulose acetate succinate, cellulose acetate phthalate, cellulose acetate butyrate, hydroxypropyl methyl cellulose phthalate, hydroxy propyl methyl cellulose acetate succinate (hypermellose acetate succinate), polyvinyl acetate phthalate (PVAP), algenic acid salt, stearic acid, shellac or a combination thereof.

15. The delayed release softgel capsule of item 14, wherein the algenic acid salt is sodium alginate, potassium alginate, or a combination thereof.

16. The delayed release softgel capsule of item 14, wherein the enteric polymer is an acrylic polymer, a methacrylic acid polymer, or a combination thereof.

17. The delayed release softgel capsule of any one of the preceding items, wherein the coating further comprises a plasticizer.

18. The delayed release softgel capsule of item 17, wherein the plasticizer comprises glyceride, triethyl citrate, or a combination thereof.

19. The delayed release softgel capsule of any one of the preceding items, wherein the pectin is in an amount of about 2.5 wt % to about 20 wt %, 5 wt % to about 18 wt %, 7.5 wt % to about 15 wt %, or about 10 wt % to about 12 wt % based on total weight of the shell composition.

20. The delayed release softgel capsule of any of items 7-9, wherein the gelatin is in an amount of about 15 wt % to about 60 wt %, about 20 wt % to about 55 wt %, about 25 wt % to about 50 wt %, about 30 wt % to about 45 wt %, or about 35 wt % to about 40 wt % based on total weight of the shell composition.

21. The delayed release softgel capsule of item 11, wherein the dextrose is in an amount of about 0.001 wt % to about 5 wt %, about 0.01 wt % to about 4.5 wt %, about 0.01 wt % to about 4 wt %, about 0.1 wt % to about 3 wt %, or about 1 wt % to about 2.5 wt % based on total weight of the shell composition.

22. The delayed release softgel capsule of any one of items 4-6, wherein the plasticizer is in an amount of about 5 wt % to about 60 wt %, about 10 wt % to about 55 wt %, about 15 wt % to about 50 wt %, about 20 wt % to about 45 wt %, or about 25 wt % to about 35 wt % based on total weight of the shell composition.

23. The delayed release softgel capsule of any of the preceding items, wherein the enteric polymer is in an amount of about 20 wt % to about 40 wt %, about 25 wt % to about 35 wt %, or about 30 wt % based on total weight of the coating.

24 The delayed release softgel capsule of item 17, wherein the plasticizer is in an amount of about 2 wt % to about 10 wt %, about 3 wt % to about 9 wt %, about 4 wt % to about 8 wt %, or about 5 wt % based on total weight of the coating.

25. The delayed release softgel capsule of any one of the preceding items, wherein the shell composition does not rupture at a pH of 1.2 at 15 minutes, 30 minutes, 45 minutes or 60 minutes when measured with a USP Apparatus II with paddles at 50 RPM, 750 ml 0.1N HCL acidic media adjusted to pH with phosphate buffer.

26 The delayed release softgel capsule of any one of the preceding items, wherein the shell composition does not rupture at a pH of between 6 and 7 at 15 minutes, 30 minutes, 45 minutes, or 60 minutes, when measured with a USP Apparatus II with paddles at 50 RPM, 750 ml 0.1N HCL acidic media adjusted to pH with phosphate buffer.

27. A process of preparing a delayed release softgel capsule of any one of the preceding items including: preparing a fill material comprising an active agent; encapsulating the fill material with a shell composition comprising pectin to form a capsule; and coating the capsule with a coating composition comprising an enteric polymer.

EXAMPLES

Specific embodiments of the invention will now be demonstrated by reference to the following examples. It should be understood that these examples are disclosed solely by way of illustrating the invention and should not be taken in any way to limit the scope of the present invention.

Coating of a Delayed Release Softgel Capsule

A batch of coated delayed release softgel capsules was manufactured according to the present disclosure. A batch of delayed release softgel capsules 1000 mg was utilized for the coating experiment. The fill material was refined fish oil containing 300 mg of Omega 3. The shell composition of the delayed release softgel capsule is summarized in Table 1.

14

TABLE 1

| Softgel Shell Composition | |
| --- | --- |
| Item Description | % (wt %) |
| Pectin | 5.0-18.0 |
| Gelatin | 25.0-48.0 |
| Dextrose | 0.01-2.20 |
| Glycerin | 8.0-22.0 |
| Sorbitol sorbitan solution | 4.0-36.0 |
| Purified Water | 5.0-18.0 |
| Total | 100.00 |

A coating composition was prepared including EUDRAGIT® FS30D, an aqueous dispersion of an anionic copolymer based on methyl acrylate, methyl methacrylate and methacrylic acid, was used for the coating polymer. The coating composition also included PlasACRYL® T20 as a plasticizer, wherein the PlasACRYL® T20 is understood as including a 20% aqueous suspension including an anti-tacking agent, a plasticizer and a stabilizer. The coating composition was prepared as a coating suspension, which is summarized in Table 2.

TABLE 2

| Coating Suspension Composition | |
| --- | --- |
| Item Description | Coating Suspension (wt %) |
| EUDRAGIT ® FS30D | 30.305 |
| PlasACRYL ® T20 | 4.545 |
| Purified Water, USP, EP | 65.000 |
| Total | 100.00 |

The delayed released fish oil softgel capsules 1000 mg were coated to achieve weight gains of 2%. The coated softgel capsules were subjected to various testing to evaluate the robustness of the enteric property. The coated capsules were also packaged into induction sealed HDPE bottles and placed on development stability under accelerated conditions per stability protocol ISS-21-047.

Comparative Coated Immediate Release Softgel Capsules

A batch of coated fish oil softgel capsules was manufactured for comparative purposes. A batch of immediate release fish oil softgel capsules 1000 mg was utilized for the coating trial. The fill material was fish oil containing 300 mg of Omega 3. The shell formula of the immediate release softgel capsule is summarized in Table 3.

TABLE 3

| Softgel Shell Formula | |
| --- | --- |
| Item Description | % (wt %) |
| Gelatin | 28.0-56.0 |
| Glycerin | 12.0-35.0 |
| Purified Water | 5.0-18.0 |
| Total | 100.00 |

15

The immediate release fish oil softgel capsule 1000 mg were coated using the same coating suspension described in Table 2 to achieve weight gains of 2% (sublot 21SC-12A) and 3.6% (Sublot 21SC-12B) respectively. The coated capsules were subjected to various testing to evaluate the robustness of the enteric property. The coated immediate release capsules were also packaged into induction sealed HDPE bottles and placed on development stability under accelerated conditions per stability protocols ISS-22-027 and ISS-22-028.

Disintegration and Rupture Tests

The coated delayed release fish oil softgel capsules 1000 mg and coated immediate release fish oil softgels 1000 mg were subjected to two stage disintegration tests and two stage rupture tests.

The disintegration tests were performed using a disintegration apparatus B, ERWEKA, Model: ZT 224. In the acidic stage, 0.1N HCl was used; in the buffer stage, pH 6.8 and pH 7.5 phosphate buffer solutions were used.

The two stage rupture tests were performed using a dissolution apparatus II, Distek, Model: 2500. In the acidic stage, biorelevant media FaSSGF with enzyme (Pepsin) pH 1.6 was used; in the buffer stage, phosphate buffer solutions with enzyme (Pancreatin) pH 7.5 was used.

The coated delayed release fish oil softgel capsules 1000 mg, coated immediate release fish oil softgel capsules 1000 mg and non-coated delayed release fish oil softgel capsules 1000 mg were also subjected to moisture absorption tests, where the capsules weight gain after exposure to various times were compared. The soaking media utilized in this study was the same acidic medium 0.1N HCl used in the disintegration tests.

Capsule Disintegration Test Results

Table 4 summarizes the burst strength data for the uncoated and 2% weight gain coated delayed release fish oil softgel capsules. The burst strength data was similar prior and after the coating step. Thus, the coating did not appear to affect the physical robustness of the delayed release softgel capsule.

TABLE 4

Burst Strength of Coated Delayed Release
Fish Oil Softgel Capsules 1000 mg

| Sample | Burst Strength (kg) | Travel Distance (mm) |
|---|---|---|
| Lot 4701394 (Uncoated) | 99.4 | 4.91 |
| 21SC-09 A (2% Weight Gain) | 110.7 | 4.74 |

Table 5 summarizes the testing results of the two stage disintegration at Time zero, right after the softgel capsules were coated.

TABLE 5

Disintegration Results of Coated Delayed
Release Softgel Capsules 1000 mg at T0

| Sample | Vessel | Disintegration Time | | | | | | Result (min) |
|---|---|---|---|---|---|---|---|---|
| | | 1 | 2 | 3 | A | B | C | |
| 21SC-09A | Acid (pH 1.2) 2 hours | Intact | Intact | Intact | Intact | Intact | Intact | Intact |
| | Buffer (pH 6.8) 1 hour | Intact | Intact | Intact | Intact | Intact | Intact | Intact |
| | Buffer (pH 7.5) | 24 min | 24 min | 22 min | 26 min | 27 min | 23 min | 24 min |

The above results show that 2% weight gain resulted in softgel capsules with robust enteric property. It is noted that the coated softgel capsules resulted in intact softgels in both pH 1.2 HCl acidic medium and pH 6.8 phosphate buffer. However, the 2% weight gain coated softgel capsules still ruptured in pH 7.5 buffer within average 24 minutes. The increased threshold pH for coated softgel capsules allows for colonic delivery of a dosage form.

Table 6 summarizes the results of the two stage disintegration at 1 month and 3 months under accelerated stability conditions (40° C./75% RH), respectively.

TABLE 6

| Disintegration Results of Coated Delayed Release Softgel Capsules 1000 mg at T1 and T3 | | | | | | | | |
|---|---|---|---|---|---|---|---|---|
| Sample 21SC-09A | | Disintegration Time (Minute) | | | | | | Result |
| (2% Weight gain) | Vessel | 1 | 2 | 3 | A | B | C | (min) |
| T = 1 M Stability | Acid (1.2) | Intact | Intact | Intact | Intact | Intact | Intact | Intact |
| (40° C./75% RH) | Buffer (6.8) | Intact | Intact | Intact | Intact | Intact | Intact | Intact |
| | Buffer (7.5) | 35 | 31 | 34 | 36 | 36 | 31 | 34 min |
| T = 3 M Stability | Acid (1.2) | Intact | Intact | Intact | Intact | Intact | Intact | Intact |
| (40° C./75% RH) | Buffer (7.5) | 42 | 41 | 43 | 43 | 44 | 44 | 43 mins |

For the coated delayed release softgel capsule with 2% weight gain (21SC-09A) at T=1 month, the softgel capsules remained intact in both pH 1.2 and pH 6.8 media and ruptured at 34 minutes in pH 7.5 buffer. At T=3 months, the coated delayed release softgel capsules stayed intact in pH 1.2 HCl medium and ruptured at 43 minutes in pH 7.5 phosphate buffer.

Table 7 summarizes the testing results of two stage disintegration at 6 months and 12 months under long term stability conditions (25° C./60% RH), 18 months intermediate stability conditions (30° C./65% RH), 6 months accelerated stability conditions (40° C./75% RH) and 22 months room temperature hold conditions.

TABLE 7

| Disintegration Results of Coated Delayed Release Softgel Capsule 1000 mg at T6 T12, T18 and T22 (with disc in buffer stage) | | | | | | | | |
|---|---|---|---|---|---|---|---|---|
| Sample 21SC-09A | | Disintegration Time (Minute) | | | | | | Result |
| (2% Weight gain) | Vessel | 1 | 2 | 3 | A | B | C | (min) |
| T = 6 M Stability | Acid (1.2) | Intact | Intact | Intact | Intact | Intact | Intact | Intact |
| (25° C./60% RH) | Buffer (7.5) | 9 | 10 | 13 | 10 | 12 | 13 | 11 min |
| T = 6 M Stability | Acid (1.2) | Intact | Intact | Intact | Intact | Intact | Intact | Intact |
| (40° C./75% RH) | Buffer (7.5) | 16 | 17 | 19 | 16 | 17 | 18 | 17 mins |
| T = 12 M Stability | Acid (1.2) | Intact | Intact | Intact | Intact | Intact | Intact | Intact |
| (25° C./60% RH) | Buffer (7.5) | 12 | 15 | 15 | 14 | 17 | 17 | 15 min |
| T = 18 M Stability | Acid (1.2) | Intact | Intact | Intact | Intact | Intact | Intact | Intact |
| (30° C./65% RH) | Buffer (7.5) | 14 | 15 | 15 | 15 | 16 | 17 | 15 min |
| T = 22 M Stability | Acid (1.2) | Intact | Intact | Intact | Intact | Intact | Intact | Intact |
| (RT Retain) | Buffer (7.5) | 10 | 11 | 12 | 10 | 10 | 12 | 11 min |

For the coated delayed release softgel capsules with 2% weight gain (21SC-09A) at T=6 months (25° C./60% RH), the softgel capsules stayed intact in pH 1.2 and ruptured at 11 minutes in pH 7.5 phosphate buffer and at T=12 months (25° C./60% RH), the softgel capsules stayed intact in pH 1.2 and ruptured at 15 minutes in pH 7.5 phosphate buffer. For T=6 months (40° C./75% RH), the delayed release softgel capsules remained intact in pH 1.2 HCl medium and ruptured at 17 minutes in pH 7.5 phosphate buffer. For T=18 months (30° C./65% RH), the delayed release softgel capsules remained intact in pH 1.2 HCl medium and ruptured at 15 minutes in pH 7.5 phosphate buffer. For T=22 months (RT Retain), the delayed release softgel capsules remained intact in pH 1.2 HCl medium and ruptured at 11 minutes in pH 7.5 phosphate buffer.

The results of the coated immediate release fish oil softgel capsules are also presented herein. Table 8 summarizes the two stage disintegration data for the coated immediate release softgel capsules with 2% weight gain and 3.6% weight gain, respectively.

The coated immediate release softgel capsule with 2% weight gain (21SC-12A) ruptured in pH 1.2 HCl medium and did not meet the requirement for enteric dosage form. The coated immediate release softgel capsule with 3.6% weight gain (21SC-12B) did not fully rupture in pH 1.2 acid medium. However, all softgel capsules released small amount of fill material, indicating insufficient enteric property.

TABLE 8

Disintegration Results of Coated Immediate Release Softgel
Capsules 1000 mg with 2% and 3.6% Weight Gain

| | Disintegration Vessel | | | | | | Results |
|---|---|---|---|---|---|---|---|
| Sample | 1 | 2 | 3 | A | B | C | Avg. (min) |
| 21SC-12 A (2% Coating) | | | | | | | |
| Acid (pH 1.2) 2 hours | Intact | Intact | Ruptured | Intact | Ruptured | Intact | Ruptured |
| Buffer (pH = 7.5) | Not performed since capsules ruptured in acid stage | | | | | | |
| 21SC-12 B (3.6% Coating) | | | | | | | |
| Acid (pH 1.2) 2 hours | Leaked | Leaked | Leaked | Leaked | Leaked | Leaked | Leaked |
| Buffer (pH = 7.5) | 22 mins | 22 mins | 22 mins | 22 mins | 22 mins | 22 mins | 22 mins |

Two Stage Rupture Tests

Table 9 summarizes the two stage rupture data for both coated delayed release softgel capsules with 2% weight gain (21SC-09A) and coated immediate release softgel capsules with 2% weight gain (21SC-12A) and 3.6% weight gain (21SC-12B), respectively.

For the coated delayed release softgel capsules with 2% weight gain (21SC-09A), the capsules stayed intact in FaSSGF with enzyme and ruptured at average 15 minutes in pH 7.5 phosphate buffer with enzyme. There were tiny oil droplets observed in 4 out of 6 vessels during the first acid stage, but the capsules stayed intact, and no further release were observed.

The coated immediate release softgel capsules with 2% weight gain (21SC-12A) and 3.6% weight gain (21SC-12B) released small amount of fill material (more than 10%) in pH FaSSGF medium with enzyme indicating insufficient enteric property.

TABLE 10-continued

| | Capsules Moisture Absorption Results of Selected softgel Capsules (Per Capsule) | | | |
|---|---|---|---|---|
| Exposure | Coated Pectin | Coated non-pectin Capsule | | Un-coated Pectin |
| Time (min) | Capsule Lot 21SC-09A | Lot 21SC-12A | Lot 21SC-12B | Capsule Lot 4701394 |
| 60 | 1.08% | −0.33% | 0.56% | 73.7% |
| 120 | 2.00% | −4.08% | −2.97% | 92.1% |

The coated delayed release softgel capsules had limited weight gain during the 120 minute soaking period, which prominently indicated strong moisture barrier provided by 2% weight gain coating and pectin shell combination. Meanwhile, both the coated immediate release softgel capsules with 2% and 3.6% weight gain started losing weight after 60

TABLE 9

Two Stage Rupture Tests Results of Coated Delayed Release Softgel Capsule with 2% weight gain and Coated Immediate Release Softgel Capsule with 2% and 3.6% weight gains

| Sample | Stage | Dissolution Vessel | | | | | | Results Avg |
|---|---|---|---|---|---|---|---|---|
| | | 1 | 2 | 3 | 4 | 5 | 6 | (min) |
| 21SC-09A (OptiGel ® DR with 2% Coating) | FaSSGF (pH = 1.6) 2 hours | Intact* | Intact* | Intact | Intact* | Intact* | Intact | Intact* |
| | Buffer (pH = 7.5) | 15 mins | 14 mins | 16 mins | 17 mins | 14 mins | 16 mins | 15 mins |
| 21SC-12 A (Immediate release with 2% Coating) | FaSSGF (pH = 1.6) 2 hours | Leaked | Leaked | Intact | Leaked | Leaked | Leaked | Leaked |
| | Buffer (pH = 7.5) | 6 mins | 6 mins | 6 mins | 4 mins | 4 mins | 5 mins | 5 mins |
| 21SC-12 B (Immediate release with 3.6% Coating) | FaSSGF (pH = 1.6) 2 hours | Leaked | Leaked | Leaked | Leaked | Leaked | Intact | Leaked |
| | Buffer (pH = 7.5) | 5 mins | 4 mins | 5 mins | 5 mins | 4 mins | 5 mins | 5 mins |

*Tiny droplets were observed.

Moisture Absorption Test

Table 10 summarizes the moisture absorption data for the 2% weight gain coated delayed release capsules, the coated immediate release softgel with 2% weight gain and 3.6 weight gain and the uncoated delayed release softgel capsules, respectively. FIG. 1 illustrates the capsule moisture absorption rate of coated capsules The moisture absorption tests was conducted by leaving the softgel capsule in an aqueous medium.

TABLE 10

| | Capsules Moisture Absorption Results of Selected softgel Capsules (Per Capsule) | | | |
|---|---|---|---|---|
| Exposure | Coated Pectin | Coated non-pectin Capsule | | Un-coated Pectin |
| Time (min) | Capsule Lot 21SC-09A | Lot 21SC-12A | Lot 21SC-12B | Capsule Lot 4701394 |
| 0 | 0.00% | 0.00% | 0.00% | 0.0% |
| 5 | 0.12% | 0.10% | 0.00% | 14.5% |
| 10 | 0.12% | 0.17% | 0.07% | 21.3% |
| 15 | 0.47% | 0.10% | 0.03% | 31.4% |
| 30 | 0.65% | 0.23% | 0.43% | 46.3% |
| 45 | 0.97% | −0.97% | 0.56% | 54.6% | minutes, which indicated the aqueous medium permeated through coating layer and dissolved non-pectin shell. The uncoated delayed release softgel capsule had more than 92% weight gain after 120 minutes which indicates strong moisture absorption.

Thus, the data shows that coating the delayed release softgel capsules with relatively low weight gains (2%) significantly improved the robustness of enteric property and minimized the moisture absorption during dissolution. Also, low weight gain coating could achieve more consistent coating uniformity, resulting in more consisting performance of the dosage forms. Additionally, coating delayed release softgel capsules with the proper enteric polymer system may broaden the application because of the increase in pH threshold to deliver the dosage form deeper into the digestive system, such as colonic delivery.

The preceding description sets forth numerous specific details such as examples of specific systems, components, methods, and so forth, in order to provide a good understanding of several embodiments of the present invention. It will be apparent to one skilled in the art, however, that at least some embodiments of the present invention may be practiced without these specific details. In other instances, well-known components or methods are not described in detail in order to avoid unnecessarily obscuring the present invention. Thus, the specific details set forth are exemplary. Particular embodiments may vary from these exemplary details and still be contemplated to be within the scope of the present invention.

Although the operations of the methods herein are described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner.

It is to be understood that the above description is intended to be illustrative, and not restrictive. Many other embodiments will be apparent to those of skill in the art upon reading and understanding the above description. The scope of the invention should, therefore, be determined with reference to the appended claims, along with the full scope of equivalents to which such claims are entitled.

What is claimed is:

1. A delayed release softgel capsule comprising:
   a fill material, wherein the fill material comprises an active agent;
   a shell composition, wherein the shell composition comprises pectin in an amount of about 2.5 wt % to about 20 wt %, based on total weight of the shell composition; and
   a coating comprising an enteric polymer comprising a combination of methyl acrylate, methyl methacrylate and methacrylic acid, wherein the coating provides a weight gain of 0.5 wt % to 3 wt % of the capsule,
   wherein the shell composition does not rupture at a pH of 1.2 at 15 minutes, when measured with a USP Apparatus II with paddles at 50 RPM, 750 ml 0.1N HCL acidic media adjusted to pH with phosphate buffer.

2. The delayed release softgel capsule of claim 1, wherein the shell composition further comprises a plasticizer.

3. The delayed release softgel capsule of claim 2, wherein the plasticizer comprises glycerol, glycerin, sorbitol, sorbitol sorbitan solution, triacetin, polysorbate, or combinations thereof.

4. The delayed release softgel capsule of claim 3, wherein the plasticizer comprises glycerin and sorbitol sorbitan solution.

5. The delayed release softgel capsule of claim 3, wherein the polysorbate comprises polysorbate 20, polysorbate 80 or combinations thereof.

6. The delayed release softgel capsule of claim 1, wherein the shell composition further comprises gelatin.

7. The delayed release softgel capsule of claim 6, wherein the gelatin is selected from the group consisting of Type A gelatin, Type B gelatin, and mixtures thereof.

8. The delayed release softgel capsule of claim 6, wherein the gelatin is selected from the group consisting of fish gelatin, hide gelatin, bone gelatin and mixtures thereof.

9. The delayed release softgel capsule of claim 1, wherein the shell composition further comprises gellan gum.

10. The delayed release softgel capsule of claim 1, wherein the shell composition further comprises dextrose.

11. The delayed release softgel capsule of claim 1, wherein the shell composition further comprises water.

12. The delayed release softgel capsule of claim 1, wherein the pectin is a low methoxy pectin.

13. The delayed release softgel capsule of claim 1, wherein the enteric polymer further comprises an acrylic polymer, cellulose acetate succinate, cellulose acetate phthalate, cellulose acetate butyrate, hydroxypropyl methyl cellulose phthalate, hydroxy propyl methyl cellulose acetate succinate (hypermellose acetate succinate), polyvinyl acetate phthalate (PVAP), algenic acid salt, stearic acid, shellac or a combination thereof.

14. The delayed release softgel capsule of claim 13, wherein the algenic acid salt is sodium alginate, potassium alginate, or a combination thereof.

15. The delay release softgel capsule of claim 13, wherein the enteric polymer is an acrylic polymer, a methacrylic polymer, or a combination thereof.

16. The delayed release softgel capsule of claim 1, wherein the coating further comprises a plasticizer.

17. The delayed release softgel capsule of claim 16, wherein the plasticizer comprises glyceride, triethyl citrate, or a combination thereof.

18. The delayed release softgel capsule of claim 6, wherein the gelatin is in an amount of about 15 wt % to about 60 wt %, based on total weight of the shell composition.

19. The delayed release softgel capsule of claim 10, wherein the dextrose is in an amount of about 0.001 wt % to about 5 wt %, based on total weight of the shell composition.

20. The delayed release softgel capsule of claim 3, wherein the plasticizer is in an amount of about 5 wt % to about 60 wt %, based on total weight of the shell composition.

21. The delayed release softgel capsule of claim 1, wherein the shell composition does not rupture at a pH of between 6 and 7 at 15 minutes, when measured with a USP Apparatus II with paddles at 50 RPM, 750 ml 0.1N HCL acidic media adjusted to pH with phosphate buffer.

* * * * *